United States Patent
Richter et al.

(10) Patent No.: US 7,595,422 B2
(45) Date of Patent: Sep. 29, 2009

(54) PROCESS FOR CONDITIONING ISOCYANATES

(75) Inventors: Frank Richter, Leverkusen (DE); Andreas Hecking, Langenfeld (DE); Martin Brahm, Odenthal (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 12/005,010

(22) Filed: Dec. 20, 2007

(65) Prior Publication Data
US 2008/0161534 A1    Jul. 3, 2008

(30) Foreign Application Priority Data
Dec. 27, 2006   (DE) ................ 10 2006 061 536

(51) Int. Cl.
*C07C 263/00* (2006.01)
(52) U.S. Cl. ............... 560/352; 528/487; 568/14; 568/8; 568/9; 568/18; 560/330
(58) Field of Classification Search ............ 560/352, 560/330; 528/480, 487, 48, 45, 51, 202; 524/139; 568/14, 8, 9, 18
See application file for complete search history.

(56) References Cited

U.S. PATENT DOCUMENTS

| 4,397,791 | A | * | 8/1983 | Krause et al. | ........... 558/112 |
| 5,260,481 | A | | 11/1993 | Scholl | ........... 560/352 |
| 6,395,925 | B1 | * | 5/2002 | Danielmeier et al. | ........ 560/352 |
| 2005/0054860 | A1 | * | 3/2005 | Osika et al. | ........... 549/57 |

FOREIGN PATENT DOCUMENTS

GB    1153815    7/1967

\* cited by examiner

*Primary Examiner*—Ling-Siu Choi
*Assistant Examiner*—Frances Tischler
(74) *Attorney, Agent, or Firm*—N. Denise Brown; Noland J. Cheung

(57) ABSTRACT

The invention relates to a novel process for conditioning isocyanates. The purpose of conditioning of isocyanates or of mixtures of isocyanates is to remove organophosphorus components in a suitable manner such that the organophosphorus compounds no longer interfere with processing of the isocyanates.

5 Claims, No Drawings

PROCESS FOR CONDITIONING ISOCYANATES

CROSS REFERENCE TO RELATED PATENT APPLICATION

The present patent application claims the right of priority under 35 U.S.C. §119 (a)-(d) of German Patent Application No. 10 2006 061 536.0, filed Dec. 27, 2006.

BACKGROUND OF THE INVENTION

The invention relates to a novel process for conditioning isocyanates.

In the production and processing of isocyanates, organophosphorus aids and additives are occasionally used. These organophosphorus aids and additives as used or in the form of secondary products, can lead to problems in the later processing of the isocyanates.

For instance, in the polyisocyanates containing uretdione groups accessible by the teaching of DE-A 1670720, for example, occasionally the oxides of the trialkylphosphines used as catalysts occur which can also be formed from other P-containing intermediates products, in particular the trialkyldihalophosphoranes. All of these P-containing species can accumulate in the process in the case of repeated use of the monomer separated off in the process typically by distillation, and this leads to problems on reuse of the monomeric isocyanate. A simple removal by distillation fails because of the catalytic activity in particular of the trialkylphosphine oxides towards isocyanates which leads to unacceptably high losses of yield having to be accepted.

There has been no lack of attempts to remove the interfering organophosphorus components in a suitable manner (i.e. conditioning of isocyanates). In these various attempts, however, it has proved that either no change of these interfering organophosphorus components occurs, or else that the isocyanate to be conditioned reacts with the conditioning agent to an unacceptable extent.

Conversion of organophosphorus compounds of the abovementioned type into phosphine sulfides by means of $P_4S_{10}$ is described, at least for some of such compounds, for example in Houben-Weil, Vol. XII/1, pp. 168 ff and literature cited therein. However, trialkylphosphine oxides are only suitable for conversion into the corresponding trialkylphosphine sulfides by means of $P_4S_{10}$ in individual cases, according to Houben-Weil, Vol. E2 (Organic Phosphorous Compounds II), pages 87 ff and literature cited therein. Where and to what extent these conversion products are inert towards NCO groups and the suitability for conversion and removal of trialkylphosphine oxides from isocyanates is not apparent from the prior art.

The object of the invention was to provide a suitable process for eliminating trialkylphosphine oxides and trialkyldihalophosphoranes from isocyanates or mixtures thereof which enables the isocyanate to be conditioned to be recovered in high yield and high purity without having the problem of interfering side reactions with the conditioning agent or its secondary products.

Surprisingly, it has now been found that treating trialkylphosphine oxide-containing isocyanates and mixtures which may be contaminated with additionally P (phosphorus) containing impurities such as, for example, trialkyldihalophosphoranes, with $P_4S_{10}$ as a conditioning agent achieves the abovementioned object.

SUMMARY OF THE INVENTION

The present invention relates to a process for the at least partial elimination of trialkylphosphine oxides and optionally trialkyldihalophosphoranes from isocyanates or isocyanate mixtures. This process comprises adding $P_4S_{10}$ to isocyanates or mixtures of isocyanates which contain trialkyphosphine oxides and optionally trialkyldihalophosphoranes, and allowing the $P_4S_{10}$ to react with the trialkyphosphine oxides and optionally trialkyldihalophosphoranes, thereby forming a proportional amount of trialkylphosphine sulfides.

DETAILED DESCRIPTION OF THE INVENTION

The trialkylphosphine oxides and trialkyldihalophosphoranes which are present in the isocyanates and isocyanate mixtures typically preferably correspond to the general formula (I):

wherein:
  R, R' and R'': may be the same or different and each represents an organic radical having 1 to 20 carbon atoms, in which heteroatoms such as oxygen, nitrogen and sulfur can be present in the chain;
  X: represents an oxygen atom in the case of trialkylphosphine oxides or a halogen atom in the case of trialkyldihalophosphoranes;
  Y: represents a halogen atom in the case of trialkyldihalophosphoranes;
  and
  n: represents 0 in the case of trialkylphosphine oxides and 1 in the case of trialkyldihalophosphoranes.

Suitable isocyanates or mixtures of isocyanates to be conditioned include all NCO-containing compounds known per se to those skilled in the art. This includes, for example, the higher-molecular-weight isocyanate secondary products which are known per se and which having a urethane, allophanate, urea, biuret, uretdione, carbodiimide, uretonimine, isocyanurate and/or iminooxadiazinedione structure.

It is preferred that the isocyanates or mixtures of isocyanates are monomeric low-molecular-weight isocyanates having $M_w \leq 500$. Examples of these include compounds such as toluene diisocyanate (i.e. TDI), naphthylene diisocyanate, 4(2)isocyanatophenylmethyl-4-isocyanatobenzene (commonly referred to as 4,4'-MDI or 2,4'-MDI), hexamethylene diisocyanate (i.e. HDI), methylpentane diisocyanate (MPDI), trimethylhexane diisocyanate (i.e. TMDI), bis(isocyanatomethyl)cyclohexane (i.e. $H_6XDI$), norbornane diisocyanate (i.e. NBDI), isophorone diisocyanate (i.e. IPDI), bis(isocyanatocyclohexyl)methane (i.e. $H_{12}MDI$) and also any desired mixtures thereof.

The amount of the $P_4S_{10}$ to be used in the process according to the invention depends primarily on the type and degree of the phosphorus-containing impurities of the isocyanate or isocyanate mixture. Such an analysis is possible without difficulty for those of ordinary skill in the art in the context of routine analyses by means of elemental analysis and/or NMR spectroscopy.

In accordance with the present invention, 0.1 to 1.0 molar of $P_4S_{10}$ are used per mole of phosphorus of the phosphorus-containing impurities present in the isocyanate or mixtures of isocyanates to be conditioned. Preferably, the ratio of $P_4S_{10}$ to the amount of phosphorius of the phosphorius-containing impurities ranges from 0.2:1 to 0.5:1.

Preferably, the process according to the invention is carried out until the proportion of the P-containing impurities, based on the amount of P-containing impurities originally present, is less than 20%, and preferably less than 10%.

The process of the invention is carried out in the temperature range 0° C. to 150° C., and preferably 40° C. to 120° C.

Subsequent to the reaction with $P_4S_{10}$, the reaction mixture including any solvent present can be purified using separation techniques which are known per se such as distillation, extraction or crystallization/filtration. If the presence of the conditioning agent and its secondary products do not interfere, the conditioned isocyanate (mixture) can also be used without further workup.

It is preferred that the first separation, subsequent to reaction with $P_4S_{10}$, is a solids separation for separating off unreacted $P_4S_{10}$ and also the insoluble conversion products from the reaction of $P_4S_{10}$ with the interfering phosphorus-containing impurities. Subsequently, a distillation proceeds, which in a preferred embodiment is a thin-film distillation.

Obviously, combinations of two or more of these separation techniques can also be employed.

It is immaterial for carrying out the process according to the invention whether the process is carried out in whole or in part batchwise or continuously.

In addition, during the process of the invention, at any desired time, additives and/or stabilizers which are customary in polyisocyanate chemistry can be also added. Examples include antioxidants, such as, for example, sterically hindered phenols (2,6-di-tert-butylphenol, 4-methyl-2,6-di-tert-butylphenol), light stabilizers, such as, for example, HALS amines, triazoles etc.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

All data on quantitative proportions (%, ppm) refer, unless stated otherwise, to the mass.

The NCO content is determined by titration as specified in DIN 53 185.

The report of mol % or of the molar ratio of different structural types to one another is based on $^{31}$P-NMR spectroscopic measurements.

The phosphorus content of all samples was determined by X-ray fluorescence analysis (XRF).

The great majority of the reactions are described by way of example using HDI as isocyanate to be conditioned. This is performed only to illustrate the advantages of the process according to the invention and is not intended to indicate a restriction of the present invention to the systems or reaction conditions described.

$P_4S_{10}$ was obtained from Aldrich, 82018 Taufkirchen, Del., commercially and used without further purification.

Example 1

According to the Invention 3 g of $P_4S_{10}$ in solid form were added to 1000 g of hexamethylene diisocyanate (HDI) which contained 360 ppm of phosphorus, over 95 mol % of the phosphorus was in the form of tributylphosphine oxide, and subsequently, the mixture was stirred for 48 h at room temperature. Part of the $P_4S_{10}$ dissolved in the course of this. Subsequently, the mixture was filtered and the filtrate was worked up by means of thin-film distillation at 0.1 mbar, wherein the evaporator temperature and metering rate were selected in such a manner that approximately 10% high-boiler run off and approximately 90% of colorless distillate were produced. The distillate contained 180 ppm of phosphorus, over 95 mol % of which was present in the form of tributylphosphine sulfide.

Example 2

According to the Invention 3.3 g of $P_4S_{10}$ in solid form were added to 1000 g of HDI which contained 580 ppm of phosphorus, approximately 50 mol % of the phosphorus was present in the form of tributylphosphine oxide and approximately 50 mol % of the phosphorus was present in the form of tributyldifluorophosphorane, and subsequently the mixture was stirred for 48 h at room temperature. Part of the $P_4S_{10}$ dissolved in the course of this. Subsequently, the mixture was filtered and the filtrate was worked up by means of thin-film distillation at 0.2 mbar, wherein the evaporator temperature and metering rate were selected in such a manner that approximately 5% high-boiler run off and approximately 95% of colorless distillate were produced. The distillate contained 210 ppm of phosphorus, over 95 mol % of which was present in the form of tributylphosphine sulfide. The signal of tributylphosphine oxide no longer occurred in the $^{31}$P-NMR spectrum, and the triplet of the tributyldifluorophosphorane was only able to be recognized at extremely low intensity.

The distillation residues (high-boiler run off) obtained in experiments 1 and 2 were highly viscous at room temperature, but could be remelted without difficulty by elevating the temperature and could be reused for conditioning after further $P_4S_{10}$ was added as additive.

Example 3

According to the Invention

A product mixture conditioned by $P_4S_{10}$ and obtained as described in Example 2 was, instead of thin-film distillation, subjected to pot-still distillation (rectification) in a packed column (evacuated, internally mirrored jacket, 50 cm long, diameter 40 mm, packed with 4 mm V4A wire spirals), wherein 99.96% (GC) pure HDI (96.4% of the total amount) having a phosphorus content <10 ppm passed overhead. The appearance of the distillation residue was completely analogous to that described under 1 and 2.

Example 4

Comparative Example

The contaminated HDI from Example 2 was, without previous pretreatment with $P_4S_{10}$, subjected to pot-still distillation (rectification) similar to Example 3, wherein, after taking off a first running (boiling point up to 74° C. at 0.2 mbar overhead pressure, 7.5% of the total amount, approximately 99.0% pure HDI), 99.9% pure HDI (59.6% of the total amount) having a boiling point 74+/−1° C. at 0.2 mbar overhead pressure and a phosphorus content <10 ppm passed over as main fraction. The bottom phase (32.9% of the total amount) became increasingly viscous in the course of the distillation and solidified after cooling to give a gel-like mass which could not be remelted, and which was only partially soluble in organic solvents and could only be isolated after breaking the glass flask. Analytically, in addition to indications of the presence of free NCO groups, principally confirmation was found for the formation of carbodiimides and uretonimines. The phosphorus content of the bottom-phase product was 110 ppm.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the at least partial elimination of trialkylphosphine oxides and optionally trialkyldihalophosphoranes from isocyanates or mixtures of isocyanates, comprising adding $P_4S_{10}$ to isocyanates or mixtures of isocyanates which contain trialkylphosphine oxides and optionally trialkyldihalophosphoranes, and allowing the $P_4S_{10}$ to react with the trialkylphosphine oxides and the trialkyldihalophosphoranes, thereby forming a proportional amount of trialkylphosphine sulfides, wherein the molar ratio of $P_4S_{10}$ to the phosphorus of the phosphorus-containing compounds present in the isocyanate or mixture of isocyanates is from 0.1:1 to 1:1.

2. The process of claim 1, wherein said trialkylphosphine oxides and trialkyldihalophosphoranes correspond to the general formula (I)

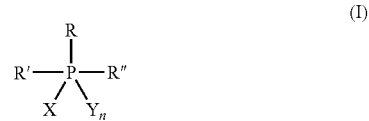

wherein:
R, R' and R'': may be the same or different and each represents an organic radical having 1 to 20 carbon atoms, in which heteroatoms such as oxygen, nitrogen and sulfur can be present in the chain;
X: represents an oxygen atom in the case of trialkylphosphine oxides or a halogen atom in the case of trialkyldihalophosphoranes;
Y: represents a halogen atom in the case of trialkyldihalophosphoranes;
and
n: represents 0 in the case of trialkylphosphine oxides and 1 in the case of trialkyldihalophosphoranes.

3. The process of claim 1, characterized in that the process is carried out until the proportion of the trialkylphosphine oxides and/or of the trialkyldihalophosphoranes is less than 10%, based on the amount of trialkylphosphine oxides and/or trialkyldihalophosphoranes originally present.

4. The process of claim 1, additionally comprising, subsequent to said reaction, separating the solids to separate off unreacted $P_4S_{10}$ and the insoluble conversion products of the reaction of $P_4S_{10}$ with the trialkylphosphineoxides and optionally, the trialkyldihalophosphoranes.

5. The process of claim 4, in which a distillation is performed subsequently to the solids separation.

* * * * *